United States Patent [19]

Mische

[11] Patent Number: 5,360,403
[45] Date of Patent: Nov. 1, 1994

[54] BALLOON CATHETER WITH LUMEN OCCLUDER

[75] Inventor: Hans A. Mische, St. Cloud, Minn.

[73] Assignee: Lake Region Manufacturing Co., Inc., Chaska, Minn.

[21] Appl. No.: 919,044

[22] Filed: Jul. 23, 1992

Related U.S. Application Data

[63] Continuation of Ser. No. 524,015, May 16, 1990, abandoned.

[51] Int. Cl.⁵ .................. A61M 29/00; A61M 5/00
[52] U.S. Cl. ............................ 604/101; 604/246; 604/256; 606/192; 606/194
[58] Field of Search ........... 604/30, 34, 43, 96–103, 604/246, 247, 167, 264; 606/192–195

[56] References Cited

U.S. PATENT DOCUMENTS

| | | | |
|---|---|---|---|
| 1,696,018 | 12/1928 | Schellberg | 604/43 |
| 2,819,718 | 1/1958 | Goldman | 604/96 |
| 2,919,697 | 1/1960 | Kim | 604/102 |
| 3,331,371 | 7/1967 | Rocchi et al. | 604/96 |
| 3,392,722 | 7/1968 | Jorgensen | 604/284 |
| 3,395,710 | 8/1968 | Stratton et al. | |
| 4,140,119 | 2/1979 | Pollack | 604/96 |
| 4,166,468 | 9/1979 | Haynie | |
| 4,240,433 | 12/1980 | Bordow | 604/96 |
| 4,406,656 | 9/1983 | Hattler et al. | 604/96 |
| 4,813,935 | 3/1989 | Haber et al. | 604/246 |
| 4,850,982 | 7/1989 | Erlich et al. | 604/96 |
| 4,932,959 | 6/1990 | Horzewski et al. | 604/96 |
| 5,085,636 | 2/1992 | Burns | 606/194 |

*Primary Examiner*—C. Fred Rosenbaum
*Assistant Examiner*—Mark Bockelman
*Attorney, Agent, or Firm*—Grady J. Frenchick

[57] ABSTRACT

An apparatus for and method of selectively occluding a lumen of a multilumen catheter during a medical procedure. The catheter may have any variety of functions of either diagnostic and/or therapeutic nature. A first open lumen to be occluded may have one or more orifices at the distal tip and/or in the side wall of the catheter for infusion of a liquid, injection of a dye, or operation of a guide wire or other control device. A small balloon adjacent the lumen to be occluded is inflated with fluid from a second, closed lumen. Whenever the small balloon is completely inflated, the first, open lumen is occluded. Whenever the small balloon is deflated, the lumen is open to the orifices distal to the small balloon.

12 Claims, 16 Drawing Sheets

BALLOON CATHETER WITH LUMEN OCCLUDER

This is a continuation application of Ser. No. 07/524,015 filed on May 16, 1990, now abandoned.

BACKGROUND OF THE INVENTION

1. Field of the Invention

The present invention relates generally to medical devices for diagnostic and therapeutic applications, and more particularly, relates to construction and use of catheters for diagnostic and therapeutic applications.

2. Description of the Prior Art

Catheters have been in general use for some time in the medical field for a wide range of applications. These include uses within the cardiovascular system, urinary tract, etc. A number of these applications are diagnostic in nature, such as the injection of dyes in angiography. Other applications are therapeutic in nature such as angioplasty. Still others simply involve the transfer of a liquid such as blood, nutrients, or pharmaceuticals.

In many catheter applications, a multilumen catheter is used wherein a first lumen is open for a portion of the procedure. A lumen is open when it has one or more orifices located near the distal end. In addition to an orifice at the tip, many infusion catheters locate the orifices along the catheter body. These orifices may provide for the transfer of a liquid, such as in a blood transfusion or urinary bladder catheterization, or may be a mechanical convenience as in a procedure wherein the catheter is slid over a previously positioned guide wire.

Most commonly, a separate lumen is employed for each function. However, it is often desirable that an open lumen also be closed for a portion of the medical procedure to permit a single lumen to perform more than one function. It is also often desirable to close an open lumen to prevent the ingress or egress of certain gases or liquids.

A prior technique for closing a lumen during a portion of a medical procedure involves using a guide wire having a seal at its distal tip to be moved in a proximal direction relative to the catheter until sealing engagement at the distal tip of the catheter is accomplished. This technique, however, requires the use of a guide wire and can usually only close a lumen which is open at the distal tip of the catheter. The seal is often less than satisfactory as well.

SUMMARY OF THE INVENTION

The present invention overcomes the problems found in the prior art by providing an apparatus for and method of occluding an open lumen of a multilumen catheter by action of an attending medical person while the catheter is within the body of the patient. This occluding occurs as a result of inflating a balloon within the open lumen from an inflation device, such as a syringe, pump, etc. located at the proximal end of the catheter. The inflation fluid is transferred to the balloon via a second, closed lumen. The balloon may be readily inflated and deflated a number of times during a medical procedure as required. These lumens may be coaxial or side-by-side.

The open lumen to be occluded may be used for the passage of a guide wire, sensor or another catheter device, or for infusion or aspiration of a fluid when open. In the closed state, the same lumen may be used for passage of a sensor or may be used to infuse or aspirate fluids through side orifices. The occlusion may occur at any position along the open lumen depending upon the location of the occluding balloon.

Similarly, the closed lumen which is used to inflate and deflate the balloon may be used for other functions. For example, the closed lumen, which inflates the balloon used to occlude the open lumen, may also be used to inflate an angioplasty balloon, a vessel occluding balloon, or a floating balloon, or may be used for the passage of connecting wires for electronic component type devices attached to the catheter shaft that embodies the aforementioned closed lumen.

A further feature of the present invention is the sharing of the closed inflation lumen with an external balloon. In this way, a single inflation operation can both occlude the open lumen and inflate an external balloon, such as a dilatation balloon.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
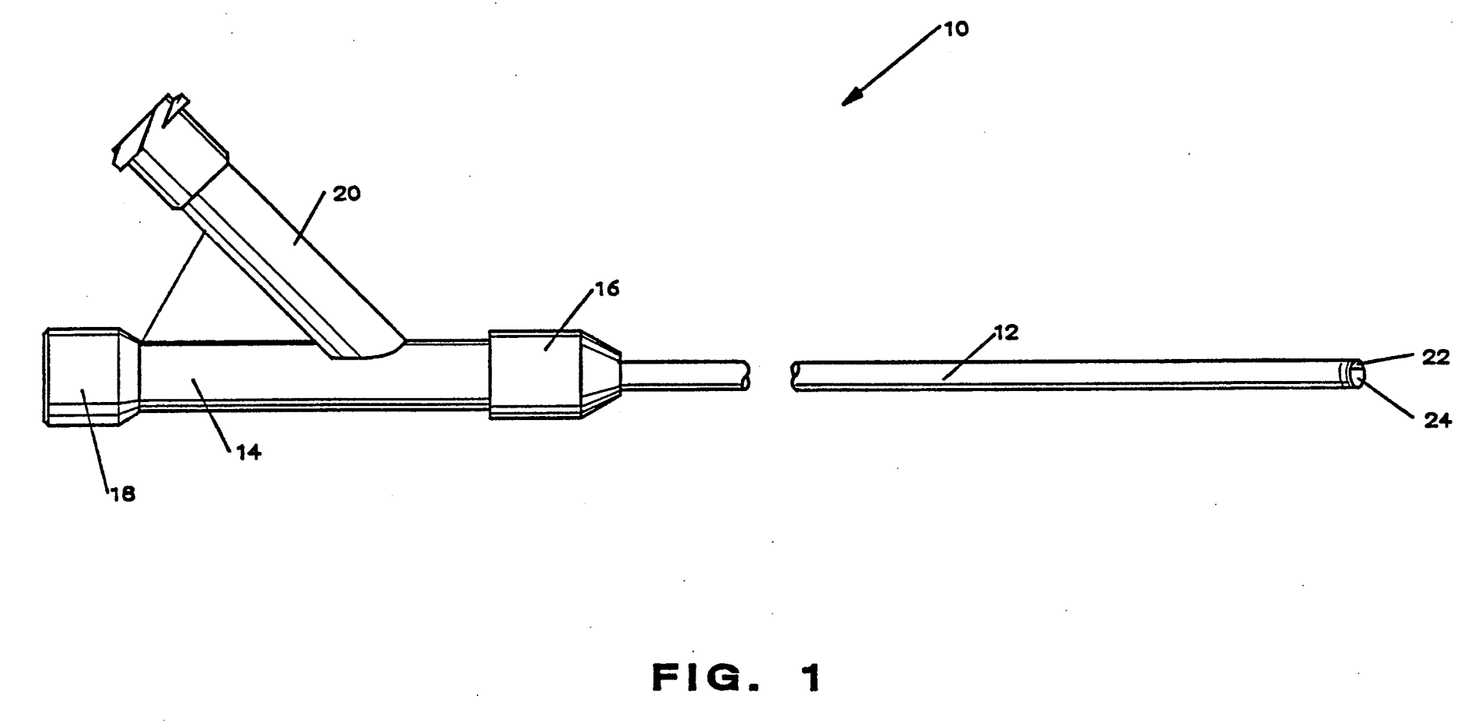
FIG. 1 is a plan view of a catheter employing the present invention.

FIG. 1 is a plan view of a catheter 10 employing the present invention. The catheter may be designed for any number of different applications within the vascular network, the urinary tract, or other body system. To be effective in the use of the present invention, however, the catheter should have at least two lumens (i.e. one lumen to be occluded and one lumen for fluid transfer to the occluding balloon) constructed in either a multilumen or coaxial lumen fashion depending upon the application. Catheter 10 in FIG. 1 may have other lumens and/or functions which are not shown for clarity.

Catheter 10 has a flexible outer sheath 12 which extends distally from rigid wye 14. Wye 14 has a main branch 18 providing fluid access to a first lumen shown open at the distal tip. Secondary branch 20 of wye 14 provides fluid access to a second lumen closed at the distal tip. Wye 14 is coupled to flexible outer sheath 12 by attachment apparatus 16. Main branch 18 can also be used to pass a guidewire.

Figure 2:
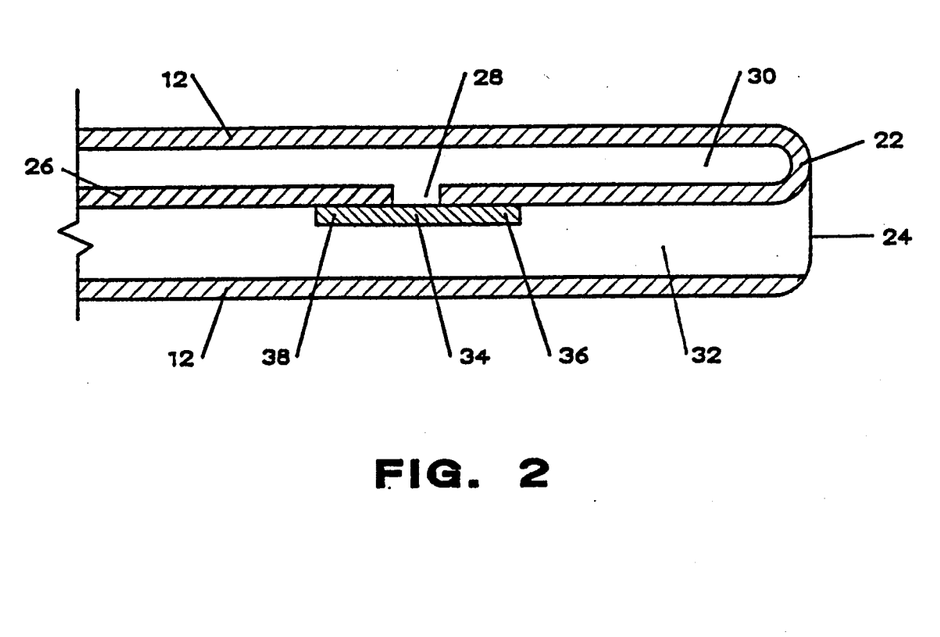
FIG. 2 is a detailed longitudinal sectioned view of the distal end of the catheter employing the present invention with the occluding balloon deflated.

FIG. 2 is a sectioned view of the distal end of catheter 10 with the occluding balloon in the deflated state. A first lumen 32 is in fluid communication with main branch 18 of wye 14 and is open at the distal tip 24 (see also FIG. 1). The second lumen 30 is divided from first lumen 32 by septum 26. As explained above, second lumen 30 is coupled to secondary branch 20 of wye 14 and is closed at distal tip 22.

Orifice 28 within septum 26 places expandable balloon 34 into fluid communication with second lumen 30. Expandable balloon 34 is attached with a fluid tight seal at points 38 and 36 as shown. To enable expandable balloon 34 to conform to the exact inner dimensions of first lumen 32, expandable balloon 34 is thoroughly elastic in nature. Because expandable balloon 34 is in fluid communication with closed lumen 30, it can be inflated using known procedures by insertion of a pressurized fluid into secondary branch 20 of wye 14.

First lumen 32 is shown open at distal tip 24. This configuration is most useful when first lumen 32 is utilized for the location of a guide wire (not shown) or for the transfer of large volumes of fluids (e.g. urinary tract). However, first lumen 32 can also be opened via one or more apertures within the sidewall of flexible outer sheath 12. This approach tends to be used for infusion of relatively small volumes of liquids (e.g. drug infusion). In either case, orifice 28 and expandable balloon 34 must be located proximal to any and all openings of first lumen 32 to permit total occlusion of the lumen.

Figure 3:
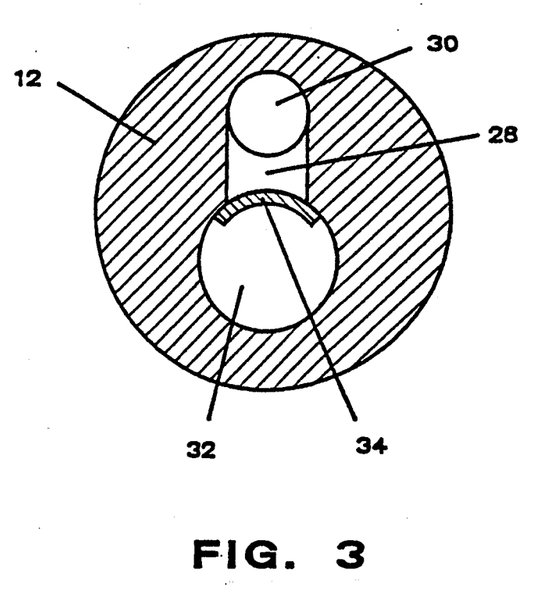
FIG. 3 is a cross sectional view of the catheter of FIG. 2.

FIG. 3 is a lateral cross sectioned view of the catheter of FIG. 2 wherein each referenced element is as previously described.

Figure 4:
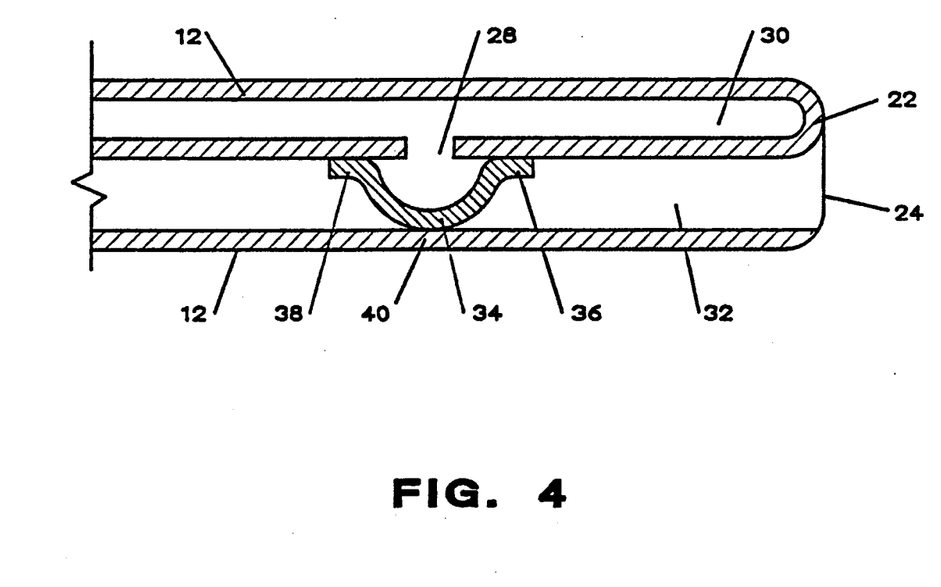
FIG. 4 is a detailed longitudinal sectioned view of the distal end of the catheter employing the present invention with the occluding balloon inflated.

FIG. 4 is a view of catheter 10 similar to FIG. 2 except that expandable balloon 34 is completely inflated. In this state, first lumen 32 is closed proximal to expandable balloon 34. This would enable medical personnel to apply first lumen 32 to a use different from when first lumen 32 is open (see also FIG. 2).

Figure 5:
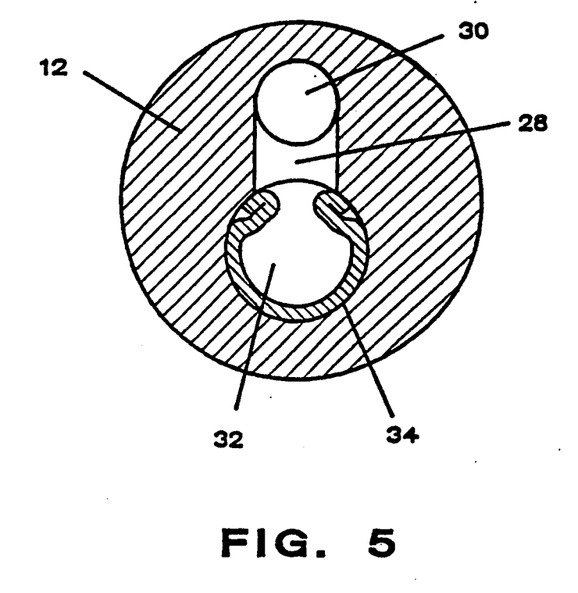
FIG. 5 is a cross sectional view of the catheter of FIG. 4.

FIG. 5 is a lateral cross sectioned view of catheter 10 in the completely inflated state. The referenced elements all correspond to the similarly referenced elements of FIG. 4.

Figure 6:
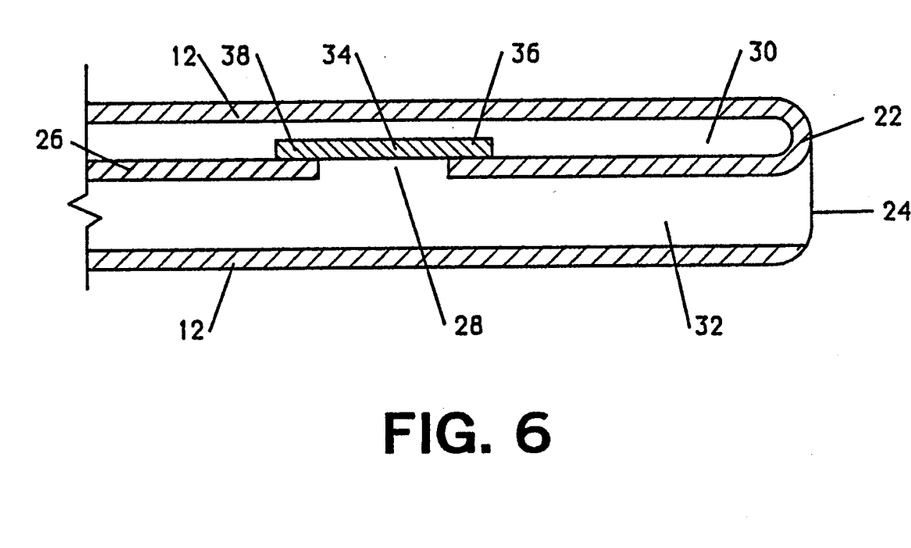
FIG. 6 is a detailed longitudinal sectioned view of the distal end of an alternative embodiment with the occluding balloon deflated.

FIG. 6 is a sectioned view of the distal end of a catheter employing an alternative embodiment of the present invention. In this embodiment, expandable balloon 34 is attached within second lumen 30 rather than first lumen 32. The operation is similar to the embodiment of FIG. 2.

Figure 7:
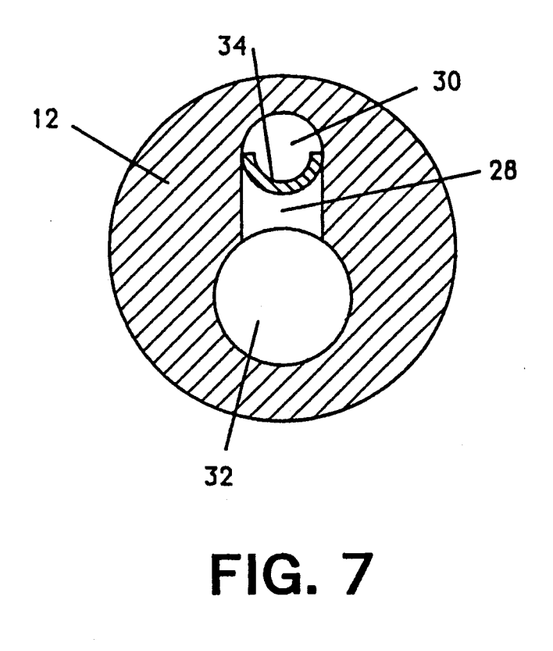
FIG. 7 is a cross-sectional view of the catheter of FIG. 6.

FIG. 7 is a lateral cross sectioned view of the catheter of FIG. 6 wherein each referenced element is as previously described.

Figure 8:
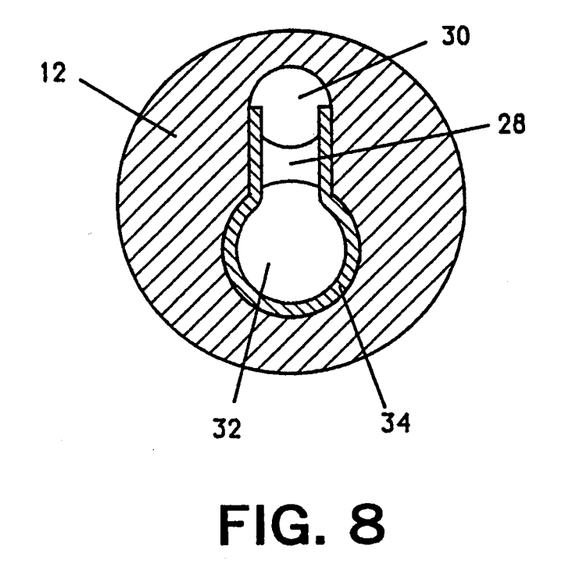
FIG. 8 is a cross-sectional view of the catheter of FIG. 7 with the occluding balloon inflated.

FIG. 8 is a lateral cross sectioned view of the catheter of FIG. 6 with expandable balloon 34 completely inflated. The referenced elements all correspond to the similarly referenced elements of FIG. 6.

Figure 9:
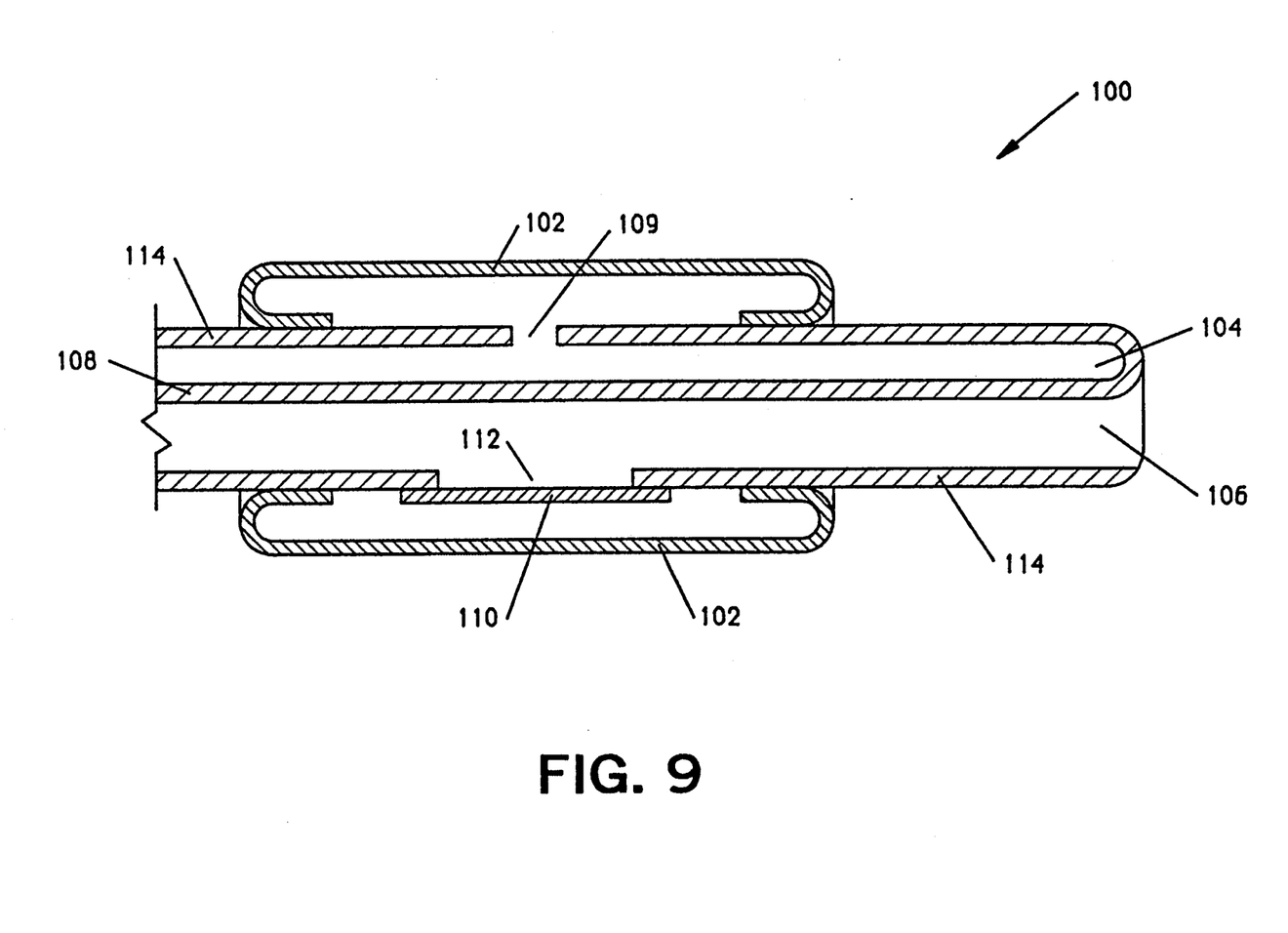
FIG. 9 is a detailed longitudinal sectioned view of the distal end of an alternative embodiment of the present invention with the balloon deflated.

FIG. 9 shows an alternative embodiment of the present invention. In the alternative embodiment, catheter 100 has an outer sheath 114. First lumen 106 is open at the distal tip and is separated from closed second lumen 104 by septum 108. In the alternative embodiment, catheter 100 has inflatable balloon 102 attached near the distal end. Inflatable balloon 102 is in fluid communication with second lumen 104 via aperture 109. Inflatable balloon 102 is inflated in the manner know in the art by injection of a pressurized fluid into the proximal end of second lumen 104 (not shown). Balloon may be inelastic as with a dilatation balloon or elastic as with a positioning device.

Inner balloon 110 is sealingly fixed over aperture 112. Because inner balloon 110 is located within inflatable balloon 102, it will tend to expand in the direction of aperture 112 as the fluid within inflatable balloon 102 is pressurized.

Figure 10:
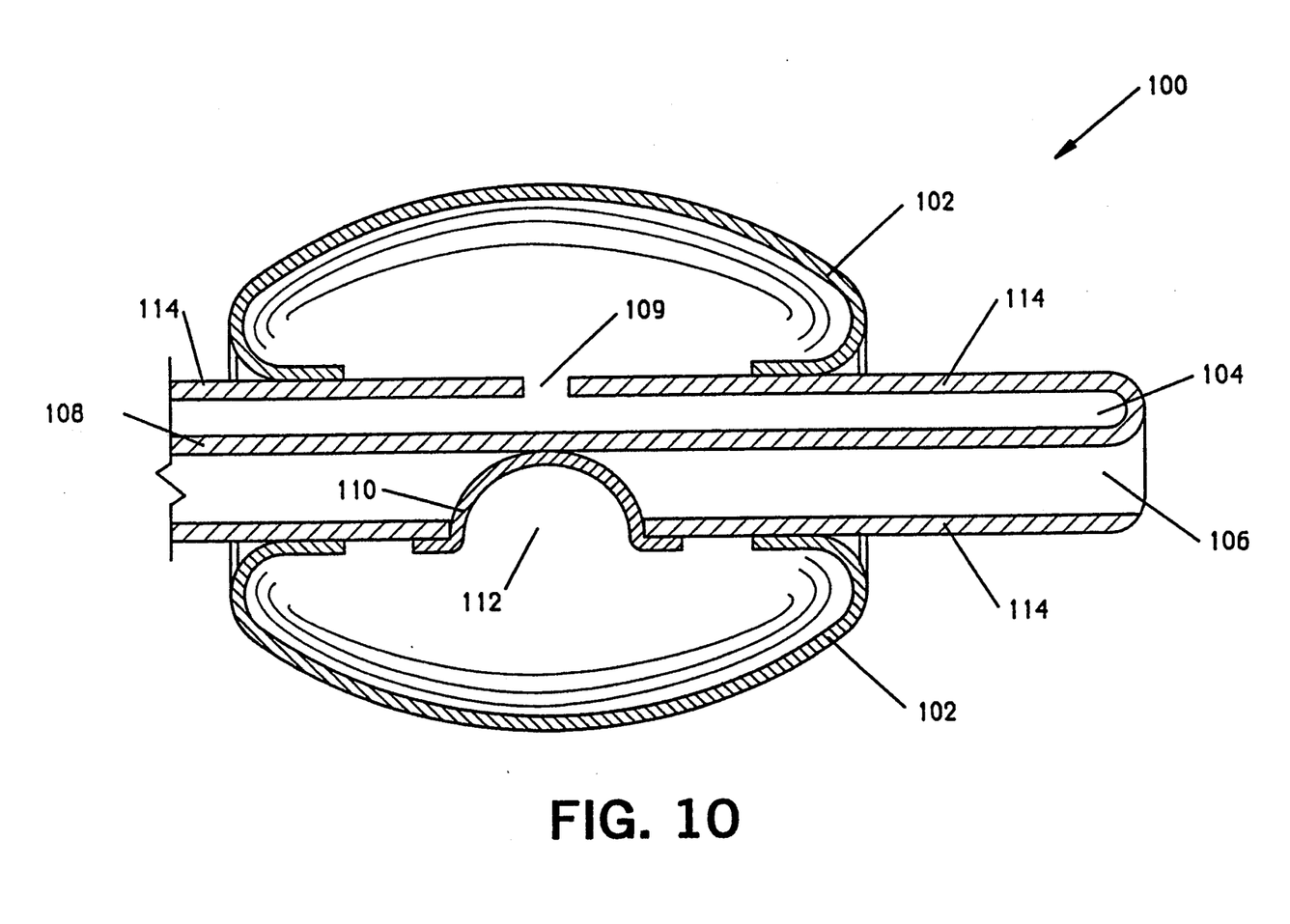
FIG. 10 is a view of the alternative embodiment of the present invention with the balloon inflated.

FIG. 10 is a view of catheter 100 similar to FIG. 9 except that inflatable balloon 102 and inner balloon 110 are inflated. Notice that first lumen 106 is occluded upon inflation of inflatable balloon 102 (and hence inner balloon 110).

Figure 11:
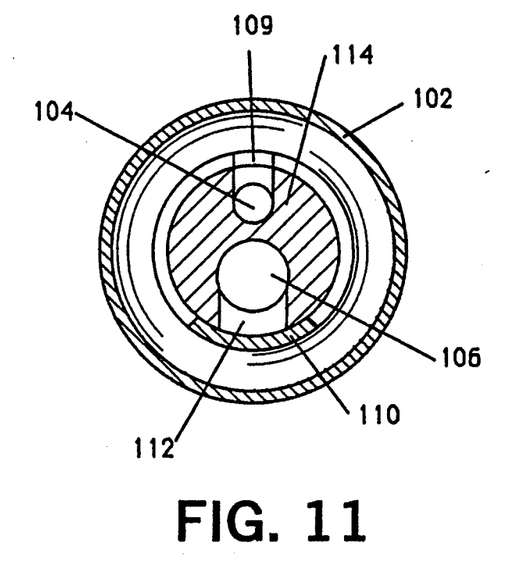
FIG. 11 is a cross sectional view of the alternative embodiment of FIG. 6.

FIG. 11 is a lateral cross sectioned view of catheter 100 in the deflated state wherein all referenced elements are as previously described.

Figure 12:
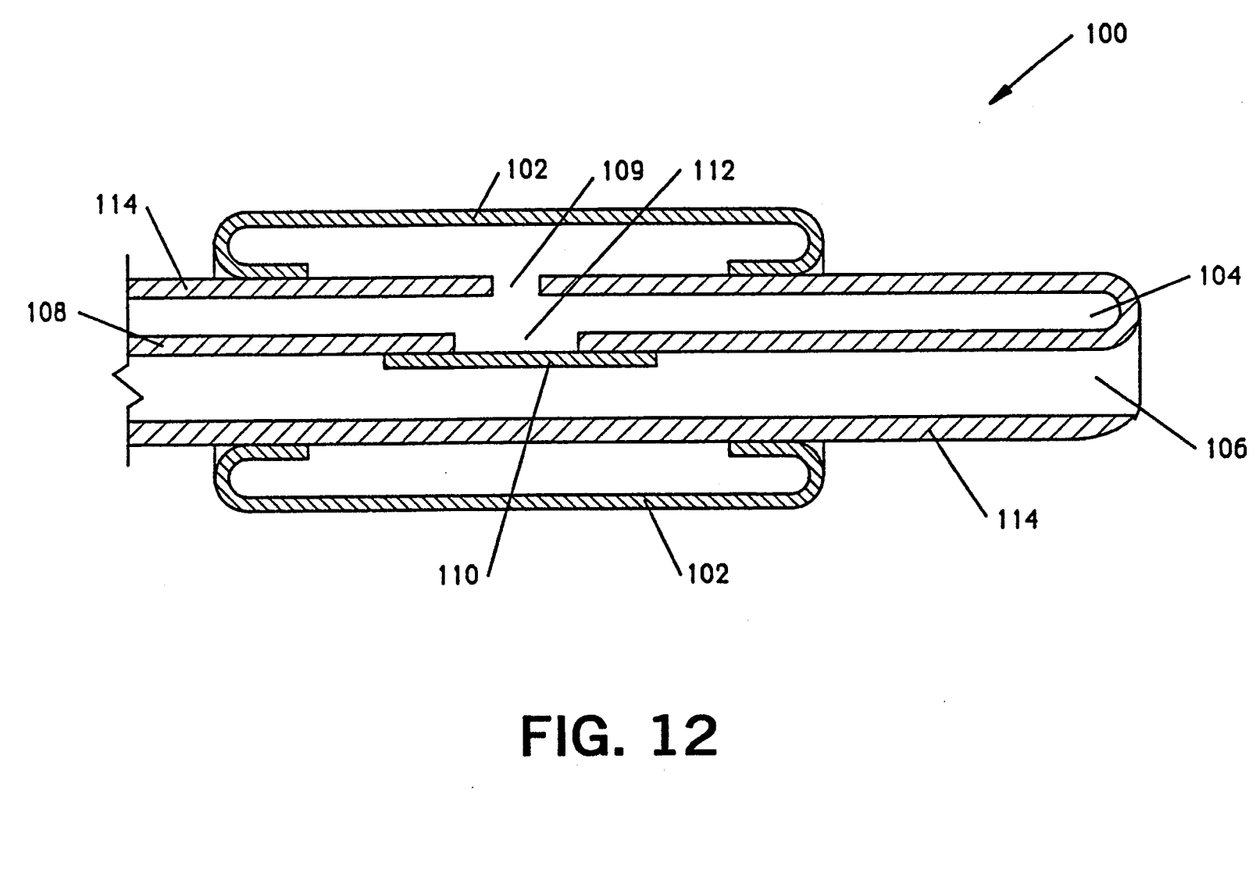
FIG. 12 is a longitudinal sectioned view of an alternative embodiment of the catheter of FIG. 9.

FIG. 12 is a sectioned view of the distal end of a catheter employing an alternative embodiment of catheter 100 of FIG. 9. All referenced elements are as previously described except that inner balloon 110 is inside rather than outside of the open lumen.

Figure 13:
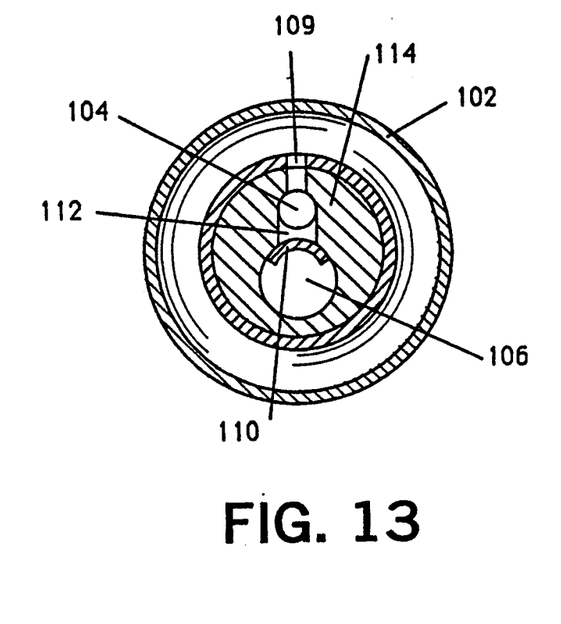
FIG. 13 is a cross-sectional view of the catheter of FIG. 12.

FIG. 13 is a lateral cross sectioned view of the catheter of FIG. 12 with inner balloon 110 deflated.

Figure 14:
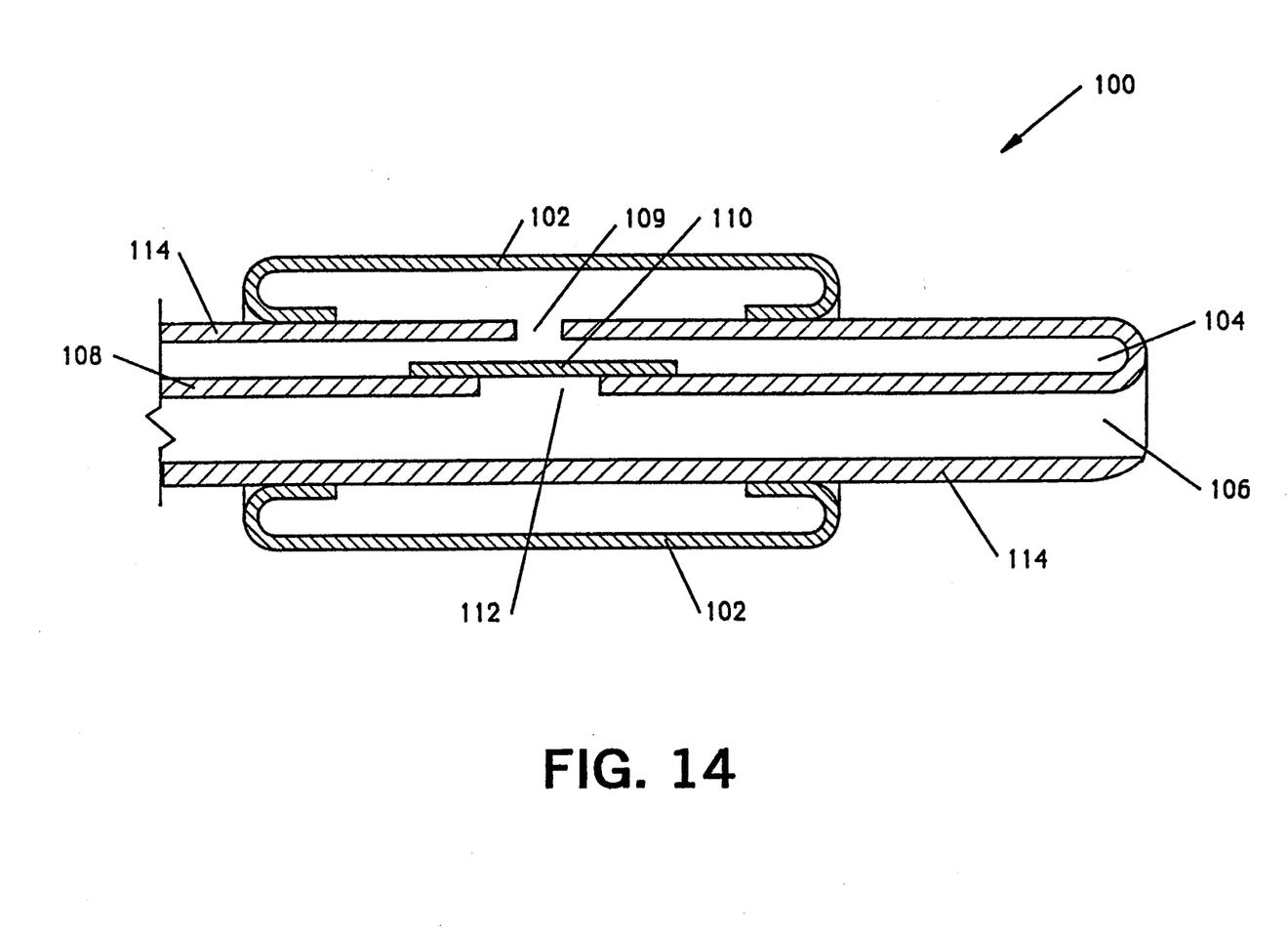
FIG. 14 is a longitudinal sectioned view of an alternative embodiment of the catheter of FIG. 12.

FIG. 14 is a sectioned view of the distal end of a catheter employing an alternative embodiment of the catheter of FIG. 12. In this embodiment, inner balloon 110 is located within closed second lumen 104 in the deflated state. Operation is as previously described.

Figure 15:
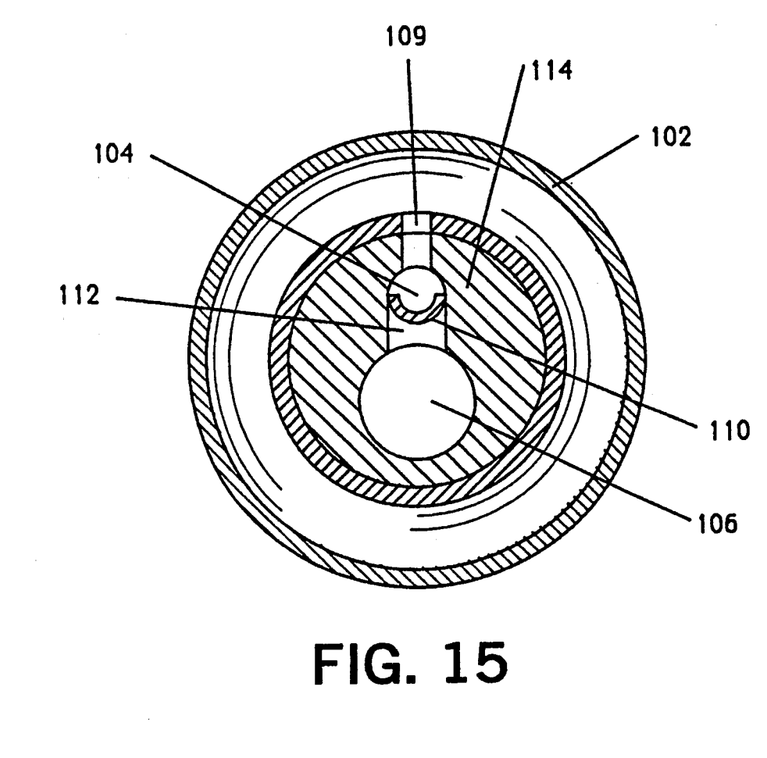
FIG. 15 is a cross-sectional view of the catheter of FIG. 14.

FIG. 15 is a lateral cross sectioned view of the catheter of FIG. 14.

Figure 16:
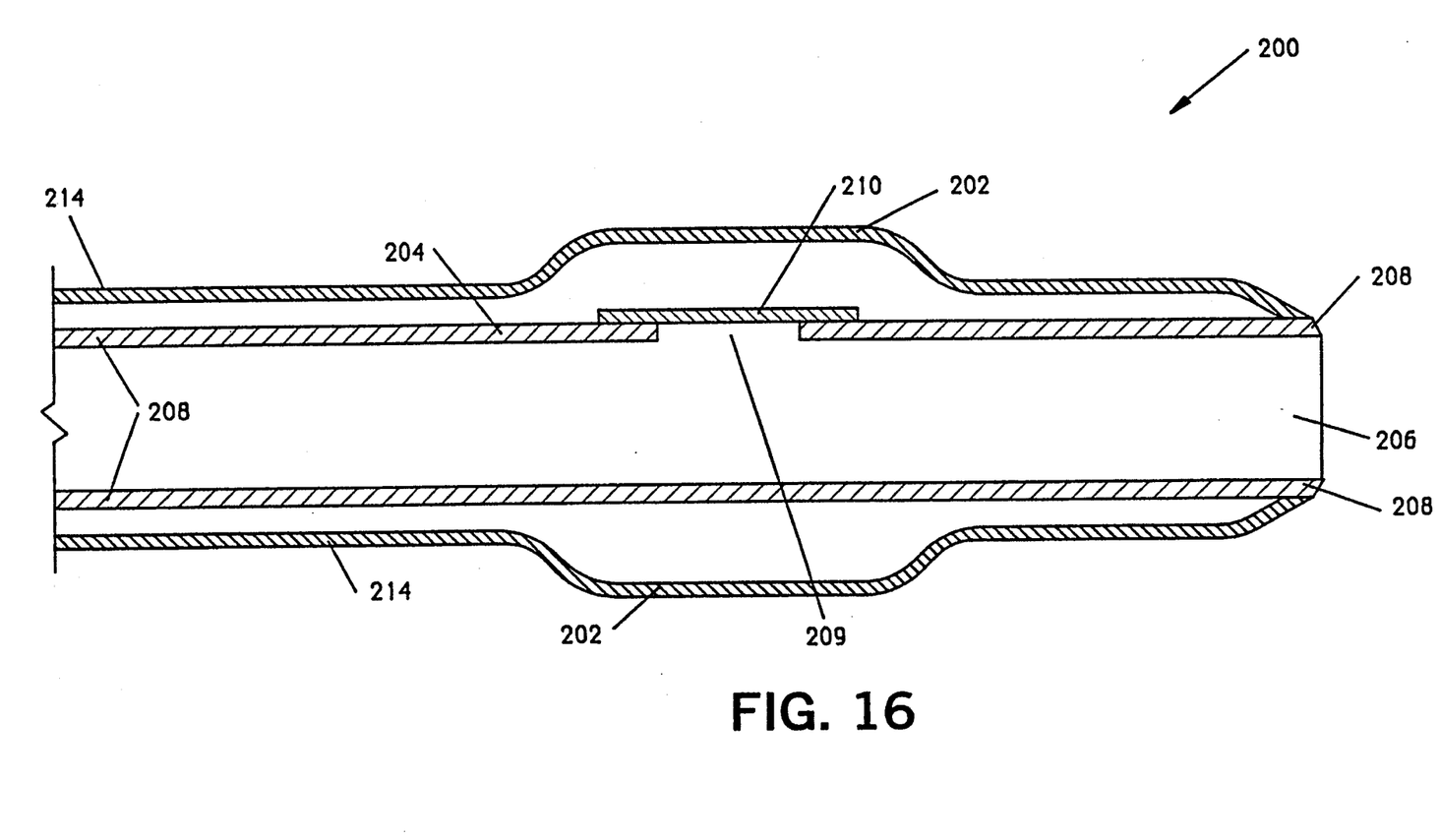
FIG. 16 is a longitudinal sectioned view of the distal tip of a coaxial catheter employing the present invention.

FIG. 16 is a sectioned view of the distal end of a coaxial catheter 200 employing the present invention. In this embodiment, inner septum 208 defines an inner lumen which is open at distal orifice 206. It may be occluded by inner balloon 210 through aperture 209. Both inner balloon 210 and outer balloon 202 may be inflated with pressurized fluid in the closed outer lumen defined by inner septum 208 and outer sheath 214. The operation of catheter 200 is similar to that of catheter 100 as previously described.

Having thus described the preferred embodiments of the present invention, those of skill in the art will readily be able to apply the teachings found herein to other embodiments without departing from the scope of the claims found herein.

I claim:

1. A method of occluding a lumen of a catheter, the catheter comprising an outer sheath confining a septum, the septum defining, with said outer sheath, a first lumen and a second lumen closed at the distal end, said first lumen having at least one opening to outside of said catheter, said catheter having a proximal end and a distal end, said first and second lumens extending from the proximal end to the distal end, said outer sheath having a first aperture in the portion thereof defining with said septum said first lumen and a second aperture in the portion thereof with said septum said second lumen, said method comprising the steps of:

a. sealing attaching an inner balloon to said outer sheath over said first aperture;

b. sealing attaching an outer balloon to said outer sheath over said second aperture and round said inner balloon; and c. inflating said inner balloon into said first lumen by inflating said outer balloon with pressurized fluid.

2. The method of claim 1, wherein said outer balloon is inflated by introducing pressurized fluid into said second lumen.

3. The method of claim 2, wherein said pressurized fluid is caused to pass into said outer balloon through said second aperture in said second lumen.

4. The method of claim 1, wherein said outer balloon is attached to said outer sheath at a point proximal to said first lumen opening.

5. A method of occluding a lumen of a catheter, the catheter comprising an outer sheath confining a septum, the septum and the outer sheath defining a first lumen and a second lumen closed at the distal end, said septum having a septum aperture, said first lumen having an opening to outside said catheter, said catheter having a proximal end and a distal end said first and second lumen extending from said proximal end to said distal end, said outer sheath having an outer sheath aperture in said second lumen, said method comprising;

a. sealing attaching an inner balloon to said outer sheath over said first aperture;

b. sealing attaching an inner balloon to said inner sheath over said septum aperture;

c. inflating said inner balloon into said first lumen by inflating said outer balloon with pressurized fluid.

6. The method of claim 5, wherein said outer balloon is inflated by introducing pressurized fluid into said second lumen.

7. The method of claim 6, wherein said pressurized fluid is caused to pass into said outer balloon through said outer sheath aperture in said second lumen.

8. The method of claim 5, wherein said outer balloon is attached to said outer sheath at a point proximal to said first lumen opening.

9. A catheter comprising:

an outer sheath, the outer sheath having distal and proximal ends and having an inner wall, said sheath having therein:

a first lumen which is open at the distal and proximal ends of the outer sheath, a second lumen which is open at the proximal end and closed at the distal end of the sheath, the first lumen and second lumens extending from the distal end to the proximal end of the outer sheath and being defined by a septum forming the inner wall of the sheath, and an outer balloon sealing arranged on said outer sheath and in fluid communication with said second lumen, and a wall portion in said first lumen defined by said outer sheath and said septum, said wall portion having an aperture with an inner balloon sealed about said aperture, said aperture positioned on said wall portion so as to be in fluid communication with the second lumen and outer balloon whereby fluid injected into said second lumen causes inflation of said inner and outer balloon members, the inner balloon member inflated into and occluding the first lumen.

10. A catheter according to claim 9 wherein the first lumen and second lumen are coaxial.

11. A catheter according to claim 9 wherein the septum is cylindrical.

12. A catheter according to claim 9 wherein the outer balloon is located at the distal end on the outer sheath, the inner balloon located within the outer balloon, the aperture in said first lumen being in fluid communication with:

a second aperture in said second lumen, said second aperture being covered by the outer balloon so as to communicate fluid to said outer balloon and said inner balloon in said wall portion.

* * * * *